(12) United States Patent
Collier et al.

(10) Patent No.: US 8,663,277 B2
(45) Date of Patent: Mar. 4, 2014

(54) BRAIDED BARBED SUTURE

(75) Inventors: John P. Collier, Franklin Lakes, NJ (US); David C. Lindh, Sr., Flemington, NJ (US); Jesse G. Nawrocki, Annandale, NJ (US); Krasimira Hristov, Bedminster, NJ (US)

(73) Assignee: Ethicon, Inc., Somerville, NJ (US)

( * ) Notice: Subject to any disclaimer, the term of this patent is extended or adjusted under 35 U.S.C. 154(b) by 1992 days.

(21) Appl. No.: 11/169,869

(22) Filed: Jun. 29, 2005

(65) Prior Publication Data

US 2007/0005110 A1    Jan. 4, 2007

(51) Int. Cl.
*A61B 17/04*    (2006.01)

(52) U.S. Cl.
USPC ........................................... 606/228

(58) Field of Classification Search
USPC ................... 606/228, 230; 602/41–43, 51
See application file for complete search history.

(56) References Cited

U.S. PATENT DOCUMENTS

| | | | | |
|---|---|---|---|---|
| 2,094,578 | A * | 10/1937 | Blumenthal et al. | 606/228 |
| 3,130,728 | A | 4/1964 | Pearson et al. | |
| 3,187,752 | A * | 6/1965 | Glick | 606/231 |
| 3,208,125 | A * | 9/1965 | Hall et al. | 28/219 |
| 3,709,263 | A * | 1/1973 | Jackson et al. | 139/420 R |
| 3,847,156 | A * | 11/1974 | Trumble | 606/231 |
| 3,981,051 | A | 9/1976 | Brumlik | |
| 4,043,344 | A * | 8/1977 | Landi et al. | 606/230 |
| 4,546,769 | A | 10/1985 | Planck et al. | |
| 4,640,178 | A * | 2/1987 | Kurzbock | 87/6 |
| 4,662,886 | A | 5/1987 | Moorse et al. | |
| 4,946,467 | A * | 8/1990 | Ohi et al. | 606/228 |
| 5,128,197 | A * | 7/1992 | Kobayashi et al. | 442/214 |
| 5,593,424 | A | 1/1997 | Northrup, III | |
| 5,683,417 | A | 11/1997 | Cooper | |
| 5,931,855 | A | 8/1999 | Buncke | |
| 5,964,783 | A | 10/1999 | Grafton et al. | |
| 6,475,229 | B1 | 11/2002 | Pagedas | |
| 6,506,197 | B1 | 1/2003 | Rollero et al. | |
| 6,645,226 | B1 * | 11/2003 | Jacobs et al. | 606/215 |
| 2003/0149447 | A1 | 8/2003 | Morency et al. | |
| 2004/0060410 | A1 * | 4/2004 | Leung et al. | 83/522.14 |

(Continued)

FOREIGN PATENT DOCUMENTS

| | | | | |
|---|---|---|---|---|
| EP | 1075843 | A1 * | 2/2001 | A61L 17/00 |
| EP | 1 075 843 | B1 | 2/2005 | |

(Continued)

OTHER PUBLICATIONS

U.S. Appl. No. 11/169,868, filed Jun. 29, 2005, titled Barbed Suture.

*Primary Examiner* — Gregory Anderson
*Assistant Examiner* — Christina Lauer

(57) ABSTRACT

A suture assembly and a method for making the same is provided. The suture assembly includes a plurality of unbarbed filamentary elements intertwined with one another and at least one barbed filamentary element having a longitudinal axis and having plurality of barbs extending outwardly therefrom in a first direction less than 90 degrees from the longitudinal axis. According to exemplary embodiments, the at least one barbed filamentary may be intertwined along its length with the plurality of unbarbed filamentary elements, and the plurality of barbs extending outwardly beyond the unbarbed filamentary elements, or the primary outer periphery of the at least one barbed filamentary element may be contained within the intertwined unbarbed filamentary elements with the plurality of barbs extending through and outwardly from the plurality of unbarbed filamentary elements.

25 Claims, 10 Drawing Sheets

(56) References Cited

U.S. PATENT DOCUMENTS

| | | | |
|---|---|---|---|
| 2004/0088003 A1* | 5/2004 | Leung et al. | 606/228 |
| 2004/0138683 A1* | 7/2004 | Shelton et al. | 606/151 |
| 2004/0237736 A1 | 12/2004 | Genova et al. | |
| 2006/0079935 A1 | 4/2006 | Kolster | |
| 2007/0038249 A1 | 2/2007 | Kolster | |
| 2007/0219587 A1 | 9/2007 | Accardo | |
| 2008/0065203 A1 | 3/2008 | Khalapyan | |
| 2008/0132943 A1 | 6/2008 | Maiorino et al. | |
| 2009/0105753 A1* | 4/2009 | Greenhalgh et al. | 606/228 |

FOREIGN PATENT DOCUMENTS

| | | |
|---|---|---|
| JP | 63-40559 A | 2/1988 |
| WO | WO 03/017850 A | 3/2003 |
| WO | WO 2004/030704 A2 | 4/2004 |
| WO | WO 2004/030704 A3 | 4/2004 |
| WO | WO 2004/030705 A2 | 4/2004 |
| WO | WO 2004/030705 A3 | 4/2004 |
| WO | WO 2006/061868 A | 6/2006 |

* cited by examiner

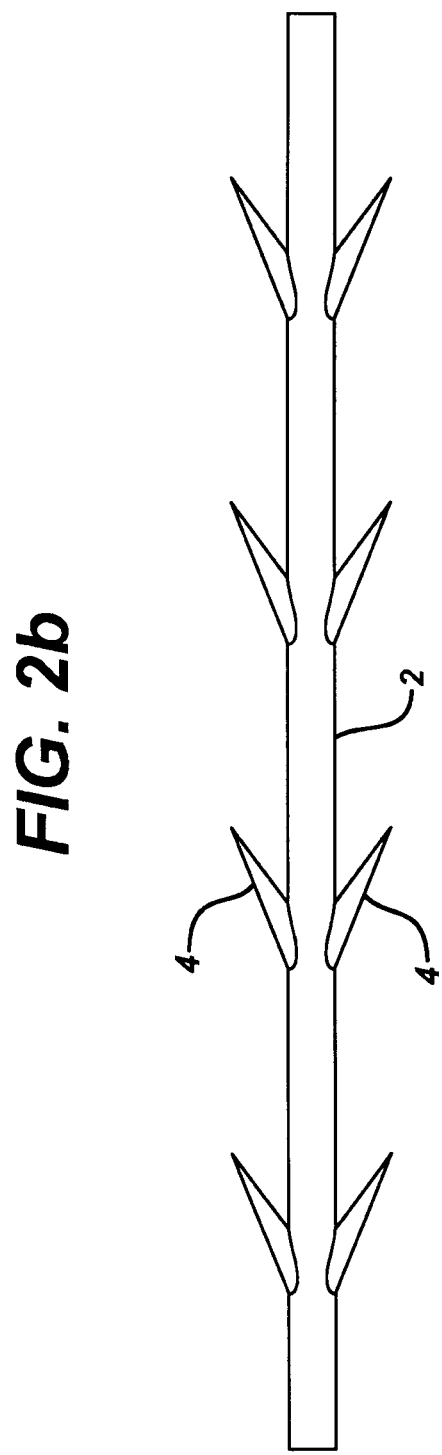

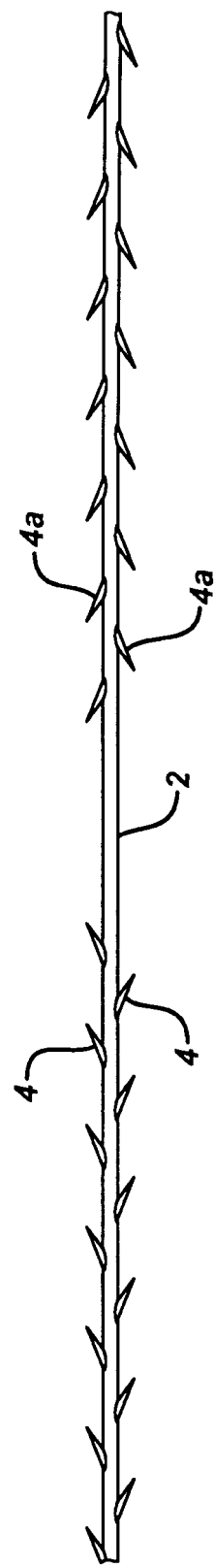

BRAIDED BARBED SUTURE

FIELD OF THE INVENTION

The present invention relates generally to the field of surgical sutures, and more particularly to a surgical suture assembly having a braided, barbed configuration.

BACKGROUND

It is well known that many wounds and surgical incisions are closed using surgical sutures of some sort. Sutures are also commonly used in many other surgical applications, such as to repair damaged or severed muscles, vessels, tissue etc. Typically, the suture is attached at one end to a needle, and the needle is drawn through the tissue to form one or more loops holding the tissue together, and subsequently tied off so that the tissue will remain drawn together. Known surgical sutures include both monofilament sutures and braided sutures. It is also known to create barbs in a monofilament suture in an effort to prevent slippage of the suture within the tissue, an example of which is described in U.S. Pat. No. 5,931,855. These monofilament barbed sutures have been used a variety of cosmetic procedures including brow and face-lifts.

Monofilament, barbed sutures, however, become increasingly prone to failure as the required holding strength needed for a particular procedure increases. Since barbed sutures are typically formed by making cuts or slits in the suture using a blade of some sort, the slits act as stress concentration points. In applications where a significant load is placed on the suture, i.e., heart valve repair or replacement procedures and orthopedic applications, a given barb may fail, or begin peeling away from the suture shaft. Once this occurs, due to the fibrous nature of the suture material the barb may be stripped off the suture shaft along a significant length of the suture causing catastrophic failure.

Monofilament sutures all require one or more knots to be tied to secure the suture in place. Knot tying is a labor-intensive, and may significantly contribute to the overall time of a surgical procedure. In addition, in some surgical procedures the existence of the knot itself may be disadvantageous. For example, in mitral valve replacement procedures, a sewing ring surrounds the new valve and is used to sew the valve in place within the valve annulus. A typical procedure may use up to 20 sutures and result in up to approximately 160 knot throws. In addition to being time consuming, this number of knots can adversely affect the profile of the ring, which can interfere with the valve function.

Thus, it would be desirable to provide a suture having an increased holding strength and/or reduces or eliminates the need for knot tying.

SUMMARY OF THE INVENTION

The present invention provides a suture assembly having a plurality of unbarbed filamentary elements intertwined with one another and at least one barbed filamentary element having a longitudinal axis and having plurality of barbs extending outwardly therefrom in a first direction less than 90 degrees from the longitudinal axis. The at least one barbed filamentary element is intertwined along its length with the plurality of unbarbed filamentary elements, and the plurality of barbs extend outwardly beyond the unbarbed filamentary elements.

Also provided is a suture assembly having a plurality of unbarbed filamentary elements intertwined with one another and having longitudinal axis, and at least one barbed filamentary element having a longitudinal axis, a primary outer periphery, and a plurality of barbs extending outwardly beyond the primary outer periphery in a first direction less than 90 degrees from the longitudinal axis thereof. The primary outer periphery of the at least one barbed filamentary element is contained within the intertwined unbarbed filamentary elements, with the plurality of barbs extending through and outwardly from the plurality of unbarbed filamentary elements.

Yet another suture assembly is provided having a plurality of unbarbed filamentary elements intertwined with one another, and at least one barbed filamentary element having a longitudinal axis and a primary outer periphery, and having a first plurality of barbs extending outwardly therefrom beyond the primary outer periphery and in a first direction less than 90 degrees from the longitudinal axis. The unbarbed filamentary elements substantially surround the primary outer periphery of the at least one filamentary element, and wherein the plurality of barbs extend outwardly beyond said unbarbed filamentary elements.

A method for making a suture assembly is also provided including forming a plurality of barbs in a filamentary element, intertwining a plurality of unbarbed filamentary elements to form an unbarbed assembly having a longitudinal axis, and inserting the barbed filamentary element through the unbarbed assembly to form a suture assembly wherein the plurality of barbs extend outwardly from the unbarbed assembly.

Yet another method for making a suture assembly is provided including forming a plurality of barbs in a filamentary element, and intertwining the barbed filamentary element with a plurality of unbarbed filamentary elements to form a suture assembly, wherein the plurality of barbs extend outwardly from the unbarbed filamentary elements.

These and other objects, features and advantages of the present invention will be apparent from the following detailed description of illustrative embodiments thereof, which is to be read in connection with the accompanying drawings.

BRIEF DESCRIPTION OF THE DRAWINGS

FIG. 2b is a side view of an alternate embodiment having aligned barbs;

FIG. 2c is a side view of another embodiment having two opposed sets of barbs;

DETAILED DESCRIPTION

Figure 1:
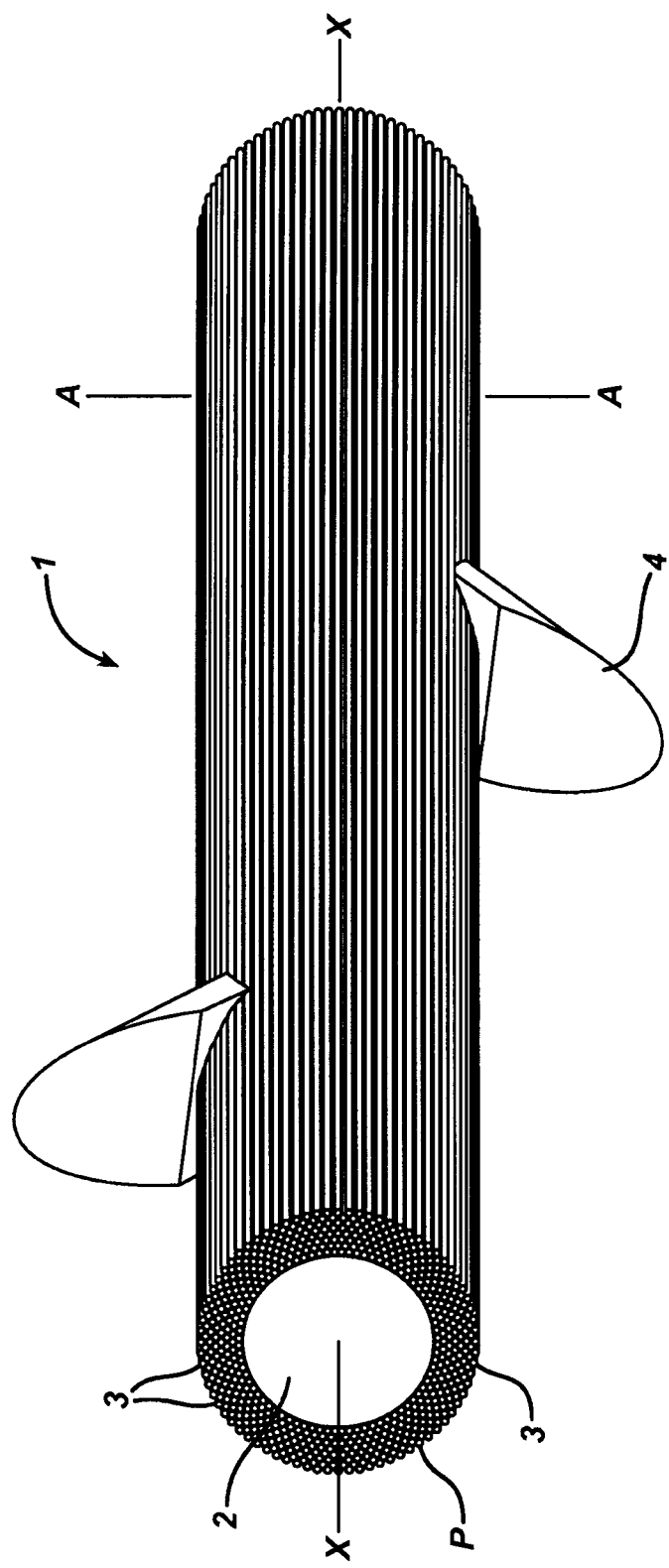
FIG. 1 is a perspective view of one embodiment of a suture assembly according to the present disclosure.

Referring now to FIG. 1, a preferred embodiment of a suture assembly 1 includes at least one barbed filamentary element 2 and a plurality of braided or intertwined unbarbed filaments 3 which will be described further below. The term "braided" is used herein to mean intertwined in any fashion. The barbed filamentary element may be made of any suitable nonabsorbable material such as polypropylene, or any suitable absorbable material such as poly(glycolide-lactide) or poly(glycolide-ε-caprolactone). Alternatively, the barbed filamentary element could be formed from a shape memory polymer, such as polyurethane-based polymers, so as to facilitate deployment of the barbs after exposure to the transition temperature of the shaped memory polymer. In the illustrated embodiment, the barbed filamentary element has a substantially larger cross-section than the unbarbed filaments, and in a preferred embodiment, the barbed filamentary element is formed from a size 0 suture and the unbarbed filamentary elements, in combination, are size 2/0 sutures. Although the barbed filamentary element is illustrated with a substantially circular cross-section, other cross sections may be used as well, such as triangular, rectangular or the like. The term "primary outer periphery" p is used herein to refer to the periphery of the cross-section of the suture assembly as if no barbs were present, such as along line A-A of FIG. 1. As shown in greater detail in FIG. 2a, the barbed filamentary element 2 lies substantially along longitudinal axis x-x, and has a plurality of barbs 4 extending outwardly therefrom in a first direction that is at an angle α relative to the longitudinal axis that is less than 90 degrees.

Figure 2A:
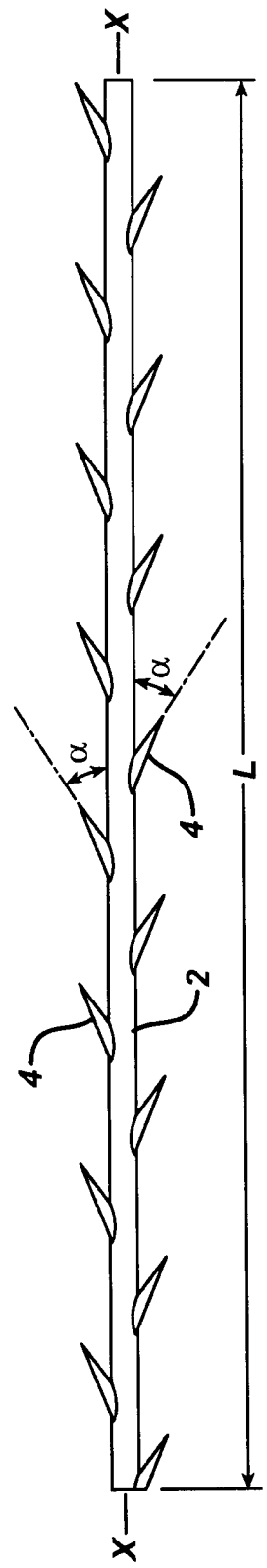
FIG. 2a is a side view illustrating one embodiment having staggered barbs.

The barbs 4 may exist along substantially the entire length L of the filamentary element 2 as shown in FIG. 2a, or along only a portion(s) of the length. Further, any suitable configuration of the barbs relative to filamentary element 2 can be used in the suture assembly of the present invention. For example, the barbs 4 may be staggered around the circumference of the filamentary element in any way (FIG. 2a) or may be aligned along the filamentary element as shown in FIG. 2b. A portion of the length of the filamentary element may also include a second set of barbs 4a facing in a second direction that is greater than 90 degrees from the longitudinal axis of the filament as shown in FIG. 2c. A use for which the configuration of FIG. 2c is advantageous will be described in greater detail below.

Figure 3:
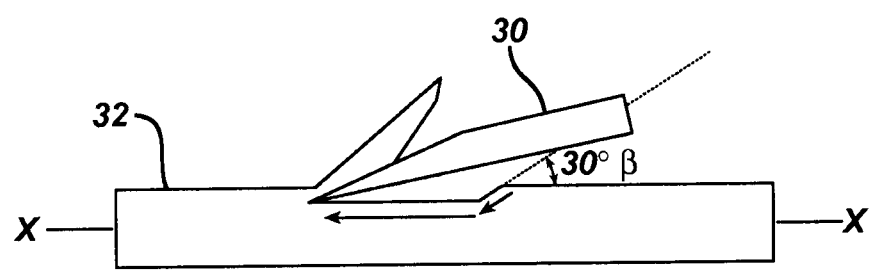
FIG. 3 illustrates cutting dimensions used to create an exemplary barb.

The barbs may be arranged on the monofilament according to any desired configuration, and can be formed using any suitable method including those well known in the art. These methods may include injection molding, stamping, cutting by knife or laser, press forming or the like. According to a preferred method, the barbs are formed by cutting a monofilament suture with any suitable cutting blade or knife. The desired number of acute, angular cuts are made directly into the suture body. FIG. 3 illustrates an exemplary cut, where the cutting blade 30 first cuts into the monofilament 32 at an angle β of approximately 30 degrees relative to the longitudinal axis x-x of the monofilament to a depth of approximately 0.08 inches, and subsequently further cuts into the monofilament for a distance of approximately 0.024 inches at an angle of approximately 0 degrees. To achieve this cutting, the monofilament is typically placed and held on a cutting vice or the like in a manner well known in the art. A template may also be used to help guide the cutting blade.

Figure 4:
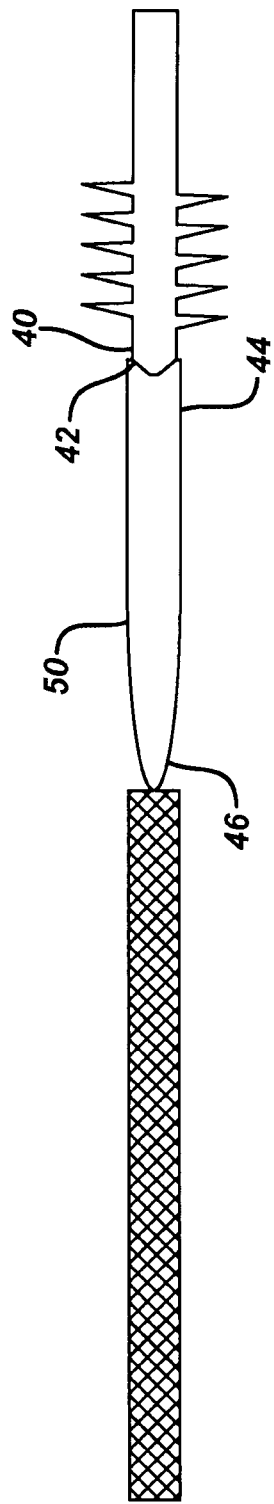
FIGS. 4-8 illustrate various steps of one method that may be used to create a suture assembly of the present disclosure.

Following creation of the barbed monofilament and the intertwined unbarbed filaments, the suture assembly 1 is formed by joining the barbed and unbarbed filaments. According to one exemplary method for accomplishing this, one end 40 of the barbed monofilament is inserted into a hollow recess 42 in the distal end 44 of a needle (opposite the pointed end 46) as shown in FIG. 4. The end 40 of the suture may be held in place within the hollow recess of the needle by any suitable means, such as by crimping the end of the needle around the suture or using adhesive or the like. Further, as an alternative, the suture end may be inserted into a cannula, sheath or any other suitable means by which to draw it through a braided suture as described below. The latter means may additionally function to protect the barbs as they are drawn through the braided filament.

Figure 5:
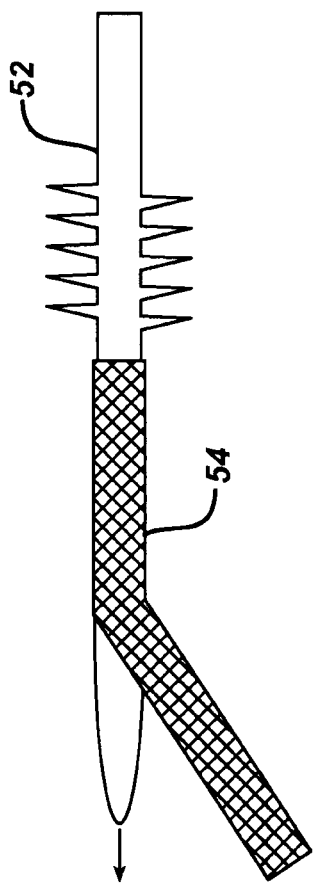
Figure 6:
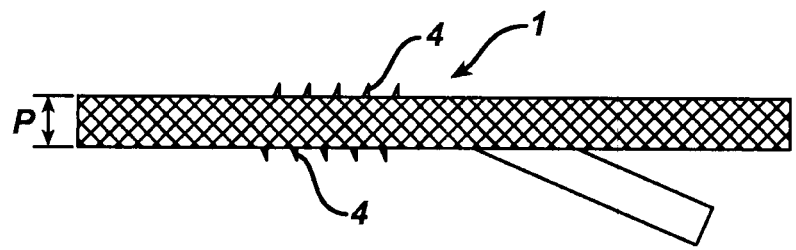
Figure 7:
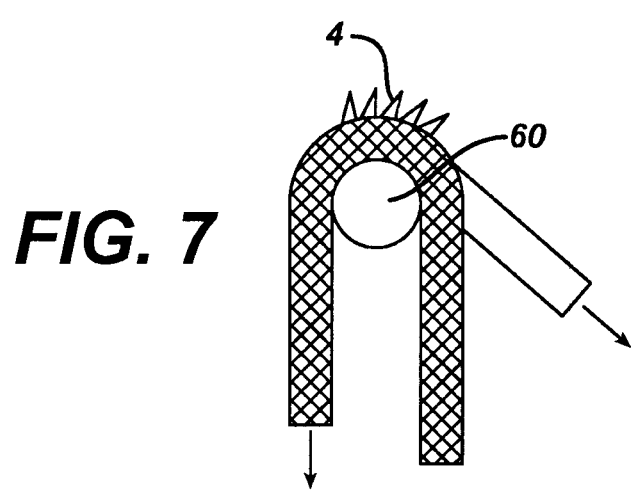
Figure 8:
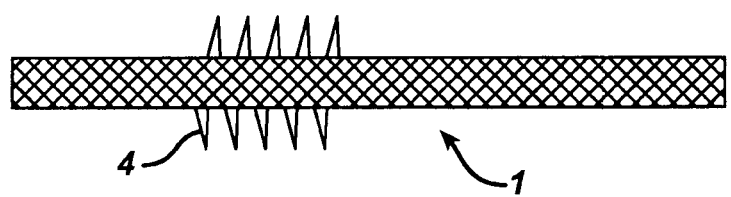

The needle 50 is then used to draw the barbed monofilament 52 through the core of the intertwined unbarbed monofilaments 54 as shown in FIG. 5. The needle (or cannula) is then removed leaving the assembly 1 as shown in FIG. 6. The barbs 4 will tend to extend outwardly from the barbed monofilament, with some extending outwardly beyond the primary outer periphery p of the intertwined unbarbed monofilaments. To further enhance the projection of the barbs, however, it may be desirable to wrap the assembly over a mandrel 60 as shown in FIG. 7. Tension is then applied as indicated by the arrows in FIG. 7, which causes the barbs to project fully as shown in FIG. 8. In order to firmly secure the ends of the barbed monofilament within the intertwined, unbarbed filaments, heat, pressure, and/or adhesive may subsequently be applied to cause bonding between them.

In an alternate embodiment, the unbarbed monofilaments may be joined with the barbed filament by braiding directly with the barbed filament, or braiding directly with a plurality of barbed filaments. To help prevent loosening of the assembly and/or to facilitate passage of the suture assembly through tissue or the like, one or more of the monofilaments can be coated or heat set to hold the assembly together. For example, heat could be applied at each end of the suture assembly using a heated die or the like. Exemplary coatings could include polyester resins or polyvinyl acetate.

The suture assemblies described above are suitable for use in a variety of surgical procedures, including those in which prosthetic devices are secured to tissue. Exemplary procedures are heart valve replacement procedures, one of which will now be described in detail. In current mitral valve replacement procedures, a surgical incision is made in the patient's chest, typically through a full median sternotomy. Cardiopulmonary bypass is then established, by inserting cannulae into the superior and inferior vena cavae for venous drainage and into the ascending aorta for arterial perfusion, with the cannulae being connected to a heart-lung machine. Once cardiopulmonary bypass and cardiac standstill have been achieved, the mitral valve is exposed by entering the left atrium and retracting the atrial tissue away using sutures or retraction devices. The atriotomy (entry incision) is usually made in the right side of the left atrium, anterior to the right pulmonary veins, although other approaches may be used.

Once access is obtained and the condition evaluated, valve replacement is performed using one of several different well known techniques to secure the prosthesis to the annulus, including interrupted mattress sutures, a continuous running suture, interrupted simple (non-mattress) sutures, or specialized clips or staples. The most common technique is the interrupted suture technique, with one such technique being illustrated in FIGS. 9a-9d. A plurality of double-needle suture assemblies 900 according to the present invention are used for the repair. As illustrated best in FIG. 9b, the suture assemblies include a first portion 910 along which a first set of barbs 912 are formed to face in one direction, and a second portion 914 along which a second set of barbs 916 face in a second direction that preferably is towards the first set of barbs.

All stitches 904 are placed through the prosthetic valve 906 before approximation of the prosthesis to the valve annulus 908. Interrupted mattress stitches using a suture assembly of the present invention, preferably of alternating color, are used. Compressed Teflon® felt pledgets 902 may be used to strengthen the repair. The mattress stitches are placed through the sewing ring of the prosthesis and then through the mitral annulus posteriorly, incorporating the chordae tendineae. The Teflon® pledgets are then threaded on separately. The initial stitches are preferably placed superiorly on the annulus, working inferiorly in a counterclockwise fashion as shown.

Figure 9A:
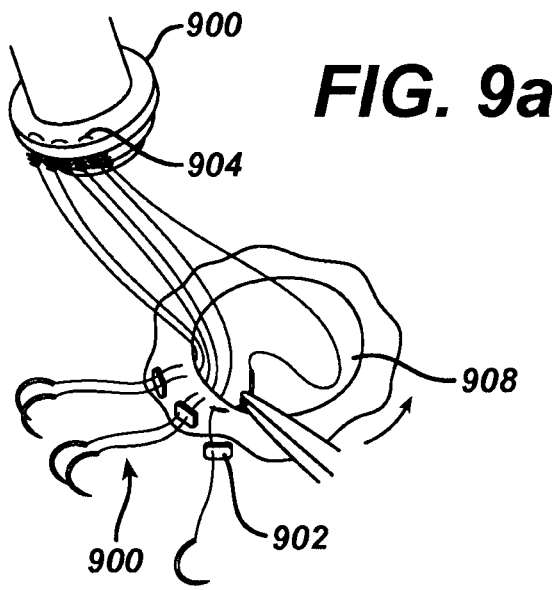
FIGS. 9a-9d illustrate various steps in an exemplary heart valve replacement procedure using a suture assembly of the present disclosure.
Figure 9B:
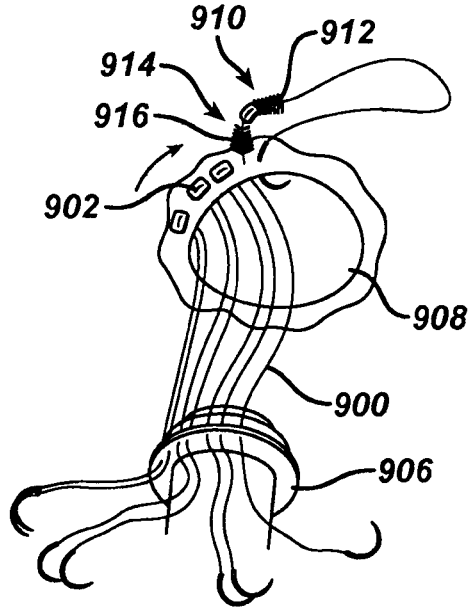
Figure 9C:
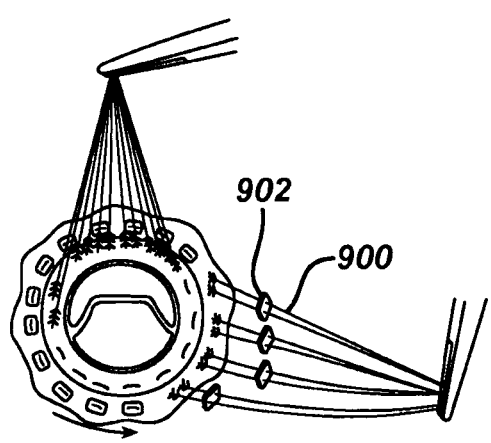
Figure 9D:
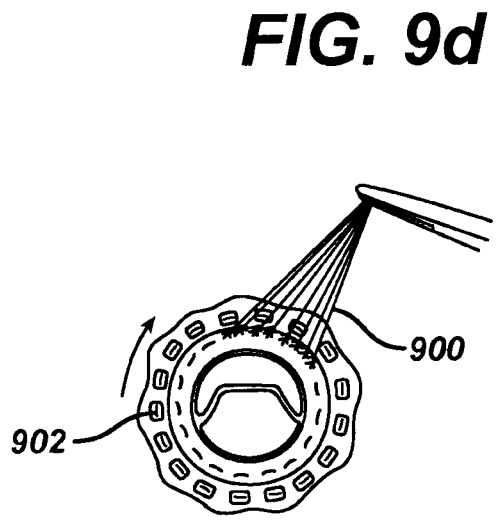

Following completion of the sutures on the posterior half of the mitral annulus, the valve prosthesis is drawn to the right side, and stitches are placed through the anterior portion of the annulus beginning superiorly and working inferiorly in a clockwise fashion as shown in FIG. 9b. The stitches are taken from the atrial surface through the mitral annulus and then brought through the sewing ring of the prosthesis. Traction on the sutures provides exposure for subsequent stitches, and Teflon® pledgets are preplaced centrally on the double needle sutures. Following placement of all sutures, strong traction is placed on the sutures as the valve prosthesis is slid over them into the annulus of the mitral valve as shown in FIG. 9c.

In traditional replacement procedures with prior art sutures, the sutures are then each tied in the same order in which they were placed, beginning posteriorly and working in a counterclockwise fashion. The anterior sutures are then tied in a clockwise fashion to complete the repair. Thus, typical mitral valve replacement procedures involve multiple suture knots, on the order of 12-16 (approximately 60 to 112 knot throws assuming approximately 5-7 throws per knot), with each knot taking approximately 20-30 seconds to perform. In addition, each knot must be secure and tightly fixate the ring to the annular tissue to avoid leakage. By utilizing a barbed suture or barbed suture assembly as described and illustrated, however, the valve replacement procedure is greatly simplified in that the time and difficulty required for knot tying is reduced. As shown, the unbarbed portions of the suture assembly ensure that the prosthetic valve can easily be parachuted into position relative to the valve annulus. Upon final positioning of the ring, however, as the prosthetic valve slides over the barbed regions of the suture assembly it becomes secure. If desired, an additional bite may be taken through the sewing ring to further secure the ring.

Figure 10:
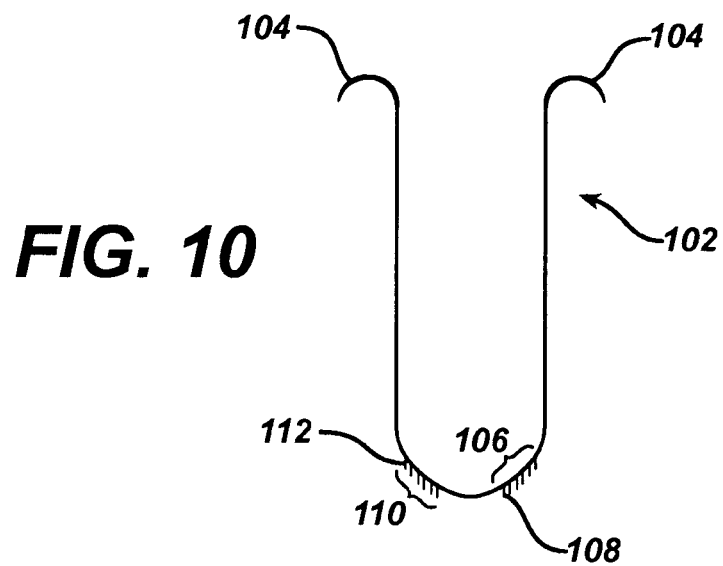
FIGS. 10 and 11 illustrate various embodiments of suture assemblies according to the present disclosure.
Figure 11:
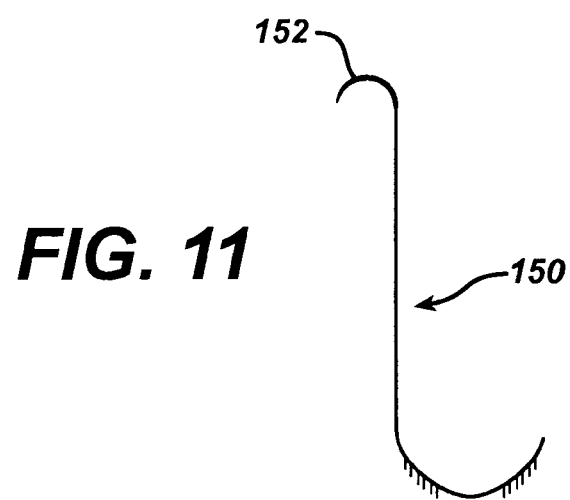

FIG. 10 illustrates in greater detail a suture assembly of the present invention that can be used, for example, in the valve replacement procedure set forth in FIGS. 9a-9d. In FIG. 10, the suture assembly 102 extends between two suture needles 104. A first portion of the length 106 includes a first set of barbs 108 that extend outwardly in a first direction and a second length 110 includes a second set of barbs 112 that extend outwardly in a second direction that is towards the first set of barbs as shown. The braided suture assembly may be formed in various ways as described above. FIG. 11 illustrates a suture assembly 150 that is attached at only one end to a single needle 152 and with no unbarbed length at the second end. In a mitral valve replacement procedure, this design would require that the surgeon pass the needle down through the sewing ring before biting through the tissue surrounding the annulus, and then subsequently pass the needle back through the ring before securing the ring against the tissue.

Figure 12:
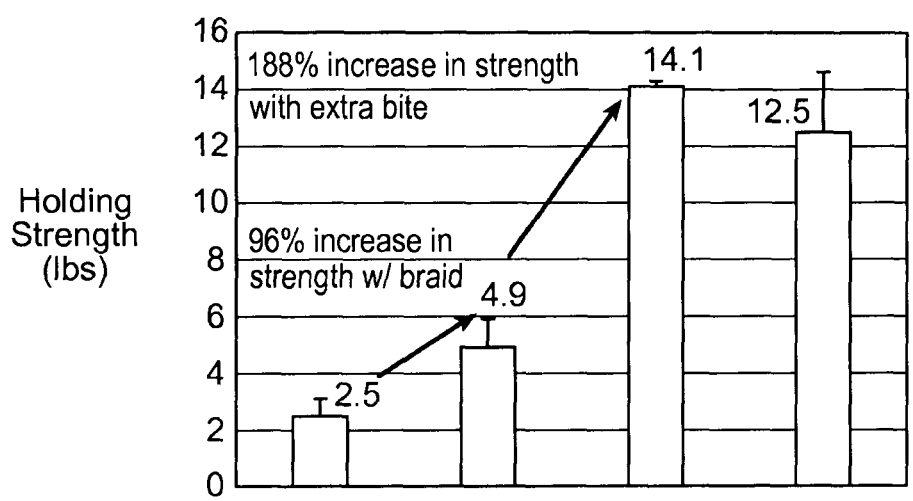
FIG. 12 is a chart illustrating relative holding strengths of a barbed suture according to the present disclosure and various other sutures.

Test results have demonstrated a significantly improved holding strength using the suture assembly of the present invention as compared to a barbed monofilament. The chart set forth in FIG. 12 illustrates these results. The first bar on the left represents the holding strength of a double-armed barbed PROLENE suture (a polypropylene suture manufactured by Ethicon, Inc. of Somerville, N.J.), size 0, when drawn straight through (perpendicular to) a DACRON® sewing ring until the barbs engage the sewing ring. Once engaged, 2.5 lbs. (+/−0.6) of force were required to dislodge the suture. The next bar represents the holding strength (4.9 lbs.+/−1.0) of a suture assembly including the same barbed suture as above, within an ETHIBOND, size 2/0, suture, which is a braided Poly (ethylene, terephthalate) suture also manufactured by Ethicon, Inc. The third bar represents the increased holding strength (14.1+/−0.2) achieved when an extra bite is taken through the sewing ring with the described suture assembly. Finally, the last bar to the right represents the holding strength (12.5+/−2.1) of an ETHIBOND, size 2/0 suture with an 8 throw knot. As can be seen, the braided, barbed suture assembly has a 96% greater holding strength as compared to the barbed monofilament, and 188% greater holding strength when one additional bite is taken. Further, with just one bite, the holding strength is greater than that of a braided suture with an 8 throw knot. Thus, superior holding strength is achieved without the time and difficulty involved with tying multiple knots.

Although illustrative embodiments of the present invention have been described herein with reference to the accompanying drawings, it is to be understood that the invention is not limited to those precise embodiments and that various other changes and modifications may be effected herein by one skilled in the art without departing from the scope or spirit of the invention.

What is claimed is:

1. A surgical suture comprising:
    a plurality of unbarbed filamentary elements intertwined with one another;
    at least one barbed monofilament element having a length extending continuously along a longitudinal axis and having a plurality of barbs extending outwardly therefrom in a first direction less than 90 degrees from the longitudinal axis;
    wherein the at least one barbed monofilament element is intertwined along its length with the plurality of unbarbed filamentary elements, and wherein the plurality of barbs extend outwardly beyond the unbarbed filamentary elements;
    and wherein the combination of barbed monofilament element and unbarbed filamentary elements collectively form a multifilament surgical suture having substantially a single longitudinal axis and adapted for surgical suture applications and having a holding strength greater than that of the at least one barbed monofilament.

2. The surgical suture according to claim 1, wherein the unbarbed filamentary elements and/or the barbed monofilament element is comprised of an absorbable material.

3. The surgical suture according to claim 1, wherein the unbarbed filamentary elements and/or the barbed monofilament element is comprised of a non-absorbable material.

4. The surgical suture according to claim 1, wherein the barbed monofilament element further comprises a second plurality of barbs extending outwardly therefrom in a second direction that is greater than 90 degrees and less than 180 degrees from the longitudinal axis.

5. The surgical suture according to claim 4, wherein the first plurality of barbs are positioned along a first predetermined portion of the length of the barbed monofilament element, and the second plurality of barbs are positioned along a second predetermined portion of the length of the barbed monofilament element, and wherein the first and second plurality of barbs are directed toward one another.

6. The surgical suture according to claim 1, wherein the plurality of barbs are staggered around a circumference of the barbed monofilament element.

7. The surgical suture according to claim 1, wherein selected ones of the plurality of barbs are aligned with one another around the circumference of the barbed monofilament element.

8. The surgical suture according to claim 1, wherein the at least one barbed monofilament element is further joined with the plurality of unbarbed filamentary element by heat setting at least first and second ends of the at least one barbed monofilament element.

9. The surgical suture according to claim 1, wherein at least one of the barbed monofilament element and/or unbarbed filamentary elements is coated with a material selected from the group consisting of polyolefins, polyesters, polyimides, polyamides, polystyrene, silicones, fluoropolymers, polyurethanes, polybutilate, expoxies, polyvinyl pyrrolidone, carboxymethylcellulose, ethylcellulose, methylcellulose, polyethylene glycol, polyvinyl alcohol, polyvinyl acetate, polybutylene terephthalate, acrylonitrile butadiene styrene, styrene acrylonitrile copolymer, styrene butadiene copolymer, and copolymers and combinations thereof.

10. The surgical suture according to claim 1, wherein the at least one barbed monofilament element is comprised of a shape memory polymer.

11. A surgical suture comprising:
a plurality of unbarbed filamentary elements intertwined with one another and having a longitudinal axis;
at least one barbed monofilament element having a length extending continuously along a longitudinal axis, a primary outer periphery, and a plurality of barbs extending outwardly beyond the primary outer periphery in a first direction less than 90 degrees from the longitudinal axis thereof;
wherein the primary outer periphery of the at least one barbed monofilament element is contained within the intertwined unbarbed filamentary elements with the plurality of barbs extending through and outwardly from the plurality of unbarbed filamentary elements;
and wherein the combination of barbed monofilament element and unbarbed filamentary elements collectively form a multifilament surgical suture having substantially a single longitudinal axis and adapted for surgical suturing applications, and having a holding strength greater than that of the at least one barbed monofilament.

12. The surgical suture according to claim 11, wherein the barbed monofilament element further comprises a second plurality of barbs extending outwardly therefrom in a second direction that is greater than 90 degrees and less than 180 degrees from the longitudinal axis.

13. The surgical suture according to claim 12, wherein the second plurality of barbs are positioned along a second predetermined portion of the length of the barbed monofilament element, and wherein the first and second plurality of barbs are directed toward one another.

14. The surgical suture according to claim 11, wherein the plurality of barbs are staggered around a periphery of the barbed monofilament element.

15. The surgical suture according to claim 11, wherein selected ones of the plurality of barbs are aligned with one another around the periphery of the barbed monofilament element.

16. The surgical suture according to claim 11, wherein the at least one barbed monofilament element is further joined with the plurality of unbarbed filamentary element by heat setting at least first and second ends of the at least one barbed monofilament element.

17. A surgical suture comprising:
a plurality of unbarbed filamentary elements intertwined with one another;
at least one barbed monofilament element having a length extending continuously along a longitudinal axis and a primary outer periphery, and having a first plurality of barbs extending outwardly therefrom beyond the primary outer periphery and in a first direction less than 90 degrees from the longitudinal axis;
wherein the unbarbed filamentary elements substantially surround the primary outer periphery of the at least one barbed monofilament element, and wherein the plurality of barbs extend outwardly beyond said unbarbed filamentary elements;
and wherein the combination of barbed monofilament element and unbarbed filamentary elements collectively form a multifilament surgical suture having substantially a single longitudinal axis and adapted for surgical suturing applications, and having a holding strength greater than that of the at least one barbed monofilament.

18. The surgical suture according to claim 17, wherein the plurality of barbs are positioned along a predetermined portion of the length of the barbed monofilament element.

19. The surgical suture according to claim 18, wherein the barbed monofilament element further comprises a second plurality of barbs extending outwardly therefrom in a second direction that is greater than 90 degrees and less than 180 degrees from the longitudinal axis.

20. The surgical suture according to claim 19, wherein the second plurality of barbs are positioned along a second predetermined portion of the length of the barbed monofilament element, and wherein the first and second plurality of barbs are directed toward one another.

21. The surgical suture according to claim 20, wherein the first and second predetermined portions of the barbed monofilament element are separated by a third predetermined portion of the length of the barbed monofilament element having no barbs projecting outwardly therefrom.

22. A method for making a surgical suture, comprising:
forming a plurality of barbs in a monofilament element;
intertwining a plurality of unbarbed filamentary elements to form an unbarbed assembly having a longitudinal axis; and
inserting the barbed monofilament element through the unbarbed assembly along said longitudinal axis of said unbarbed assembly to form a suture assembly wherein the plurality of barbs extend outwardly from the unbarbed assembly to thereby form a multifilament surgical suture having substantially a single longitudinal axis and adapted for surgical suturing application, and wherein the suture assembly has a greater holding strength that that of the barbed monofilament element.

23. A method for making a surgical suture, comprising:
forming a plurality of barbs in a monofilament element;
intertwining the barbed monofilament element with a plurality of unbarbed filamentary elements to form a suture assembly wherein the plurality of barbs extend outwardly from the unbarbed filamentary elements to thereby form a multifilament surgical suture having substantially a single longitudinal axis and adapted for surgical suturing applications,
wherein the suture assembly has a holding strength greater than that of the barbed monofilament element.

24. The method according to claim 23, wherein the intertwining step comprises braiding the barbed monofilament element with the plurality of unbarbed filamentary elements.

25. The method according to claim 23, wherein the barbed monofilament element has a primary outer periphery with the barbs extending outwardly beyond the primary outer periphery, and wherein the intertwining step comprises intertwining the plurality of unbarbed filamentary elements around the barbed monofilament element so as to substantially surround the primary outer periphery of the barbed monofilament element, but wherein the plurality of barbs extend through the unbarbed filamentary elements and outwardly therefrom.

* * * * *